United States Patent [19]

Sabel et al.

[11] Patent Number: 4,883,666

[45] Date of Patent: Nov. 28, 1989

[54] CONTROLLED DRUG DELIVERY SYSTEM FOR TREATMENT OF NEURAL DISORDERS

[75] Inventors: Bernhard A. Sabel, Munich, Fed. Rep. of Germany; Andrew Freese, Jamaica Plain; William M. Saltzman, Somerville, both of Mass.

[73] Assignee: Massachusetts Institute of Technology, Cambridge, Mass.

[21] Appl. No.: 43,695

[22] Filed: Apr. 29, 1987

[51] Int. Cl.⁴ .......................... A61F 13/00; A61K 9/14
[52] U.S. Cl. ..................................... 424/422; 424/423; 424/425; 424/426; 424/486; 424/487
[58] Field of Search ............... 424/426, 423, 425, 490, 424/473, 422, 486, 487

[56] References Cited

U.S. PATENT DOCUMENTS

| | | | |
|---|---|---|---|
| 3,625,214 | 12/1971 | Higuchi | 128/260 |
| 3,832,252 | 8/1974 | Higuchi | 424/433 |
| 3,880,991 | 4/1975 | Yolles | 424/432 |
| 3,948,254 | 4/1976 | Zaffaroni | 424/426 X |
| 3,965,255 | 6/1976 | Bloch et al. | 424/450 |
| 3,976,071 | 8/1976 | Sadek | 424/425 |
| 4,069,307 | 1/1978 | Higuchi | 424/432 |
| 4,177,256 | 12/1979 | Michaels | 424/432 |
| 4,217,898 | 8/1980 | Theeuwas | 424/433 |
| 4,263,273 | 4/1981 | Appelgren et al. | 424/490 X |
| 4,278,087 | 7/1981 | Theeuwes | 424/426 X |
| 4,351,337 | 9/1982 | Sidman | 424/426 X |
| 4,391,797 | 7/1983 | Folkman et al. | 424/425 |
| 4,675,189 | 6/1987 | Kent et al. | 424/490 |

FOREIGN PATENT DOCUMENTS

| | | | |
|---|---|---|---|
| 0168862 | 1/1986 | European Pat. Off. | 424/426 |
| 0226061 | 6/1987 | European Pat. Off. | |
| 2167662 | 6/1986 | United Kingdom | 424/425 |

OTHER PUBLICATIONS

Cardinal, John R., *Medical Applications of Controlled Release*, "Matrix Systems", vol. I, pp. 41–67, 87–89 CRC Press Inc. (1984).

A. D. Schwope, et al., *Chemical Abstracts* 84, 304 Abstract No. 84:184849x.
R. Willette, *Chemical Abstracts* 84(13) 304 Abstract No. 184855w (Jun. 28, 1976).
Suzuki and Price, *Journal of Pharmaceutical Sciences* 74(1) 21–24 (Jan. 1985).
Sladek, et al., *J. Neurosurg.* 68,337–351 (1981).
Cotzias, et al., *New Eng. J. Med.* 276(7) 374–379 (Feb. 16, 1967).

(List continued on next page.)

Primary Examiner—Thurman K. Page
Attorney, Agent, or Firm—Kilpatrick & Cody

[57] ABSTRACT

The present invention is a method and composition for treatment of ischemic, metabolic, congenital, or degenerative disorders of the central or peripheral nervous system. The composition is formed by encapsulation within an implantable biocompatible polymeric device of one or more compounds which have the effect or replacing or stimulating functions of the nervous system. A variety of biocompatible polymers including both biodegradable and non-degradable polymers can be used to form the implants. An essential feature of the composition is linear release, achieved through manipulation of the polymer composition and form. The selection of the shape, size, drug, polymer, and method for implantation are determined on an individual basis according to the disorder to be treated and the individual patient response. A plethora of neurally active substances can be used to treat or manipulate neurological disorders, including Parkinson's Disease, particularly the subset which is refractory or poorly responsive to existing therapies; Alzheimer's Disease; Huntington's Disease; and trauma, such as spinal cord injury.

22 Claims, 9 Drawing Sheets

OTHER PUBLICATIONS

Yahr, et al., *Arch. Neurol.* 21,343–354 (Oct. 1969).
Rossor, et al., *J. Neurolog. Sci.* 46,385–392 (1980).
Juncos, et al., *Neurol* 37,1242–1245 (Jul. 1987).
Juncos, et al., *J. Neurol. Neurosurg. Psych.* 50,194–198 (1987).
Quinn, et al., *Lancet* 412–415 (Aug. 21, 1982).
Shoulson, *Neurol.* 25,1144–1148 (Dec. 1975).
Cedarbaum, *Neurol.* 37,1607–1612 (Oct. 1987).
Mouradian, et al., *Ann. Neurol.* 22,475–479 (1987).
Martin, *JAMA* 216(12),1979–1983 (Jun. 21, 1971).
Tolosa, et al., *Neurol.* 25,177–183 (Feb. 1975).
Nutt, *Ann. Neurol.* 22,535–540 (Mar. 3, 1987).
Mars, *Arch. Neurol.* 23,91 (Feb. 1973).
Juncos, et al., *Arch Neurol.* 44,1010–1012 (Oct. 1987).
Bergmann, et al., *Adv. Neurol.* 45,463–467 (1986).
Brady, *Molecular Basis of Lysosomal Storage Disorders* 461–474 (Academic Press 1984).
Pincus, et al., *Arch. Neurol.* 44,1006–1009 (1987).
Saarinen, et al., *Acta Neurol. Scandinav.* 58,340–349 (1978).
Birket-Smith, et al., *Lancet* 431–432 (Feb. 24, 1973).
Cedarbaum, et al., *Neurol.* 37,233–241 (1987).
Curzon, et al., *Lancet* 781 (Apr. 7, 1973).
Woods, et al., *Lancet* 1391 (Jun. 16, 1973).
Chase, et al., *Adv. in Neurol.* 45,477–480 (1986).
Juncos, et al., *J. Neurol. Neurosur. Psych.* 50,194–198 (1987).

CONTROLLED DRUG DELIVERY SYSTEM FOR TREATMENT OF NEURAL DISORDERS

BACKGROUND OF THE INVENTION

This invention is generally in the area of treatments of neural disorders and is in particular a method and composition for controlled drug delivery to neurological sites.

Problems with the nervous system due to injury, disease and congenital defects are widespread. The treatment of brain and spinal cord damage is one of the major goals in modern neurology. The causes for brain damage are many, including direct trauma due to physical insults, stroke as a result of hemorrhage or vascular occlusion, neuronal degeneration due to inherited metabolic and neurochemical dysfunction, and aging.

Unfortunately, few effective treatments currently exist. There are a number of approaches to treatment of the behavioral problems resulting from brain lesions. One option utilizes the brain's own capacity for restoration. For example, when additional transmitter precursor is made available to the neurons, there is an increase in transmitter synthesis by the brain.

The most successful form of treatment presently available for Parkinson's disease takes advantage of this principle. The behavioral symptoms, which are containing neurons, can be reduced by systemic application of L-dopa, a biosynthetic precursor of dopamine. The efficacy of therapy with L-dopa is due to its ability to pass the blood-brain-barrier, unlike dopamine. The blood-brain-barrier normally prevents most molecules from passing from the circulatory system into the brain.

Although L-dopa therapy is very effective in many cases, there are several problems associated with this therapy. There is a subset of patients, including those patients in advanced stages of the disorder, which are refractory or poorly responsive to L-dopa therapy. Furthermore, the "once-a-day" (or several times a day) treatment with L-dopa which results in pulsed rather than constant drug levels, in combination with the variation between patients with respect to drug absorption patterns, causes phasic swings of the symptom reduction and the patient's mood state during the course of the day.

The surprising lack of effective treatment for most nervous system injury has resulted in a search for novel approaches to the problem of manipulating brain damage. Two recently explored techniques are the use of tissue transplants into damaged brain, and peripheral or central injections of compounds which are believed to enhance regeneration or outgrowth of neural tissue.

Two types of tissue have been transplanted: fetal tissue and adrenal medullary tissue. The fetal brain transplants are based on experimental results showing that implantation of developing nerve tissue obtained from rat fetus and implanted into brain-damaged host animals reduces behavioral deficiencies due to the lesions. Some preliminary trials implanting adrenal medullary tissue into the brain were recently performed in human patients with Parkinson's disease in Sweden, Mexico, and, as of April 1987, the United States. The result was a reduction of some behavioral abnormalities. Anatomical studies currently underway to determine the physiological basis of the behavioral effects indicate that transplants do not function by establishing appropriate new axonal connections with the host tissue, but rather by the non-specific release of neurotransmitters ("trickling") and/or release of neurotrophic substances that promote neurite outgrowth, which may improve survival of, and possibly regenerate, partly damaged neurons.

From an ethical point of view it is difficult to conceive how human fetal tissue can be used clinically. The use of adrenal tissue also presents several problems, including the fact that the adrenal gland preferentially releases epinephrine (a metabolite of dopamine) rather than dopamine itself. In any case, if the non-specific release of transmitter and/or neurotrophic factors is the underlying mechanism of fetal or other tissue implants, and these factors can be identified and isolated or manufactured, it would be more reasonable to apply these substances directly to the brain in a controlled, sustained manner.

Neurotrophic substances play a number of potential therapeutic roles in other neurological disorders. One of the mechanisms by which the brain repairs itself following brain damage is through the regeneration and sprouting of new neuronal connections. It has recently been shown that injections of growth promoting, neurotrophic substances enhance the rate and extent of regeneration in the brain and bring about an enhanced degree of behavioral recovery in brain damaged animals. For example, gangliosides, which are able to cross the blood brain barrier, have been demonstrated to be effective for treating brain damage and are being used for the treatment of peripheral nerve disorders in Europe. Intracerebral injections of Nerve Growth Factor (NGF), a protein, also reduces behavioral deficits. Unfortunately, with the exception of gangliosides, all neurotrophic substances discovered so far, including NGF and similar substances which may be able to retard cell death in the brain, are large molecular weight molecules unable to pass through the blood-brain-barrier.

The inability of large molecular weight molecules such as proteins to cross the blood brain barrier is also a major problem in the potential use of enzyme replacement therapies for the treatment of lysosomal storage diseases such as Tay Sachs and Gaucher's disease and for the recently discovered use of beta interferon to reduce the frequency and severity of multiple sclerosis attacks. The beta interferon was administered directly into the spinal column in the initial clinical trials. Due to a number of side effects and discomfort to the patients, it is desirable to have another method of administration.

Various slow release polymeric devies have been developed in recent years for the controlled delivery of drugs, foods and pesticides. Using these devices, drugs can be released at constant, predictable rates in the human body. In comparison to traditional drug delivery methods, such as pills or injections, slow release polymeric devices have some distinct advantages. For example, it is thereby possible to maintain constant drug levels in the blood. Slow release polymers also provide a means for localized drug administration. Most drugs taken orally or otherwise must migrate throughout the entire body to reach their site of action. This often requires a high systemic dose to achieve the necessary local dose. With controlled-release implants, a continuous local level of drug can be maintained without distribution to other tissue or organs, where it could cause harm. By eliminating the high initial drug levels associated with conventional dosage forms, and maintaining drug levels in a therapeutically desired range, one can minimize side effects. Controlled drug delivery also reduces the need for follow-up care since a single controlled release dose can last for long periods of time. Other advantages include the preservation of volatile medications and drugs that are rapidly metabolized by the body, which must otherwise be given in high quantities and multiple doses. Controlled-release systems can protect the drug from degradation and allow it to be continuously released in unaltered form. This is particularly important for substances that are very expensive.

Another problem alleviated by controlled release compositions is in the handling and administration of the drug by the patient. Patient compliance is often difficult to achieve, particularly with a neurological disease such as Parkinson's disease, where depression and intellectual deterioration are common.

For these reasons, it is desirable to provide a controlled drug release system for use in treating nervous system disorders. Despite the use of controlled drug delivery systems in the treatment of a variety of diseases, including malignancy, and metabolic defects such as diabetes, it has never been directly applied to the treatment of nonmalignant nervous disorders, including ischemic, metabolic, congenital or degenerative disorders, wherein the purpose is to replace lost function or prevent defective function. This is despite the fact that the technology for encapsulating bioactive compounds within a polymeric device has been known for a long time and people have suggested that such devices might be useful for treatment of nervous disorders.

There are a number of reasons why this technology has not been successfully reduced to practice, including the complexity of the nervous system, the difficulties in delivery of substances to the nervous system, especially the brain, and the differences in response of individual patients to drugs delivered locally at a constant rate and dosage rather than in discrete doses via the circulatory system. An example of a prior art polyanhydride drug delivery device is taught by U.S. Pat. No. 3,625,214 to Higuchi. This device consists of a spirally wound layer of biodegradable polymer overlaid with drug which is released as the polymer degrades. Although it is noted that a variety of configurations can be used to achieve a desired release pattern, there is no teaching of how to treat neural disorders where the goal is to replace or supplement the biological function of the cells, not just to introduce a substance having a particular effect when administered by conventional means.

The nervous system is complex and physically different from the rest of the body. There are two "systems", the central nervous system and the peripheral nervous system. As used in the present invention, "nervous system" includes both the central (brain and spinal cord) and peripheral (nerves, ganglia, and plexus) nervous systems. The peripheral nervous system is divided into the autonomic and somatic nerves. The somatic nerves innervate the skeletal muscles and the autonomic nerves supply the innervation to the heart, blood vessels, glands, other visceral organs, and smooth muscles. The motor nerves to the skeletal muscles are myelinated, whereas the postganglionic autonomic nerves are generally nonmyelinated. The autonomic nervous system is further divided into the sympathetic and the parasympathetic nerves. In general, the sympathetic and parasympathetic systems are viewed as physiological antagonists. However, the activities of the two on specific structures may be different and independent or integrated and interdependent.

As is readily apparent, both the physical differences and interrelatedness of these components of the nervous system must be taken into account in designing a drug delivery system. As stated in *The Pharmacological Basis of Therapeutics,* edited by Gilman et al, on page 10 (MacMillan Publishing Company, NY 1980)

"The distribution of drugs to the CNS from the blood stream is unique, mainly in that entry of drugs into the CNS extracellular space and cerebrospinal fluid is restricted . . . Endothelial cells of the brain capillaries differ from their counterparts in most tissues by the absence of intercellular pores and pinocytotic vesicles. Tight junctions predominate, and aqueous bulk flow is thus severely restricted . . . The drug molecules probably must traverse not only endothelial but also perivascular cell membranes before reaching neurons or other drug target cells in the CNS . . . In addition, organic ions are extruded from the cerebrospinal fluid into blood at the choroid plexus by transport processes similar to those in the renal tubule. Lipid-soluble substances leave the brain by diffusion through the capillaries and the blood-choroid plexus boundary. Drugs and endogenous metabolites, regardless of lipid solubility and molecular size, also exit with bulk flow of the cerebrospinal fluid through the arachnoid villi . . . The blood-brain barrier is adaptive in that exclusion of drugs and other foreign agents such as penicillin or dtubocurarine protects the CNS against severely toxic effects. However, the barrier is neither absolute nor invariable. Very large doses of penicillin may produce seizures; meningeal or encephalitic inflammation increases the local permeability."

There are other problems. The immune system does not function within the CNS in the same manner as it does in the tissues and corporeal systems. A representative example of the problems in treating nervous system disorders is in the treatment of bacterial meningitis with antibiotics. Very toxic and high concentrations of the drugs are required.

As a result of the complexity of the nervous system and the physical differences as compared to other body organs and tissues, it has not been possible to design a system for drug delivery to the nervous system that is safe and effective, particularly prior to actual implantation in vivo in a human patient followed by long term observation.

It is therefore an object of the present invention to provide a system for use in treating disorders of both the central nervous system and the peripheral nervous system.

It is another object of the present invention to provide a system which is safe and does not raise serious ethical considerations.

It is a further object of the present invention to provide a system for treatment of nervous system disorders which is economical, practical and decreases problems with patient compliance.

It is yet another object of the present invention to provide a predictable system for direct, sustained, and linear application of drugs to the nervous system which can be modified as necessary to accomodate variations between patients with respect to the treatment required.

SUMMARY OF THE INVENTION

The present invention is a composition formed by encapsulation of one or more compounds within an implantable biocompatible polymeric device for treatment of ischemic, metabolic, congenital, or degenerative disorders of the central or peripheral nervous system.

A plethora of neurally active substances can be used to treat or manipulate neurological disorders. Among these disorders are Parkinson's Disease, particularly the subset which is refractory or poorly responsive to existing therapies, treatable with encapsulated dopamine or L-dopa implanted within the brain, or a combination of L-dopa and carbidopa encapsulated in a polymer and implanted within the periphery; Alzheimer's Disease, treatable by implants of a polymer containing choline, acetylcholine or cholinergic agonists or neuronotrophic agents; Huntington's Disease, potentially treatable by implants of a polymer containing such excitatory amino acid neurotransmitter antagonists as MK801; and trauma, such as spinal cord injury, potentially treatable by polymer implants containing repair or growth enhancing substances, such as gangliosides.

Other neurological and psychiatric disorders, such as schizophrenia, depression, and epilepsy, could potentially be treated by the application of slow-release technology containing relevant drugs to the nervous system, either by a direct implantation into the nervous system or by implantation into the periphery.

A variety of biocompatible polymers including both biodegradable and non-degradable polymers can be used to form the implants. A key criterion in forming the implant is a design which results in linear release over a sustained period of time and which can be readily removed for modification or in case of an undesirable response by the patient. Another is the use of a method for encapsulation which does not decrease the bioactivity of the compound. The selection of the shape, size, drug, polymer, and method for implantation are determined on an individual basis according to the disorder to be treated and the individual patient response.

The success of the method is demonstrated in animal models using controlled drug delivery of neuroactive substances such as dopamine or L-dopa encapsulated in ethylene vinyl acetate polymers. Linear release of gangliosides from EVA devices through geometric manipulations is also shown.

DETAILED DESCRIPTION OF THE INVENTION

The device of the present invention, a polymeric controlled drug delivery device for treatment of nervous disorders, was developed to address the following needs: (1) to maintain constant, rather than phasic, levels of exogenously supplied substances having an effect on the nervous system; (b 2) to reduce problems with patient compliance while avoiding ethical problems; (3) the desire to circumvent the blood-brain barrier, when necessary, which often prevents access to the brain of active substances using more conventional methods of drug delivery; and (4) to better target substances to given regions of the brain or peripheral nervous system.

Current applications of slow release technology include the controlled drug delivery of insulin and contraceptives. One of the drug delivery polymers, ethylene vinyl acetate (EVA), has now been approved by the Food and Drug Administration (FDA) for use in humans.

Figure 1A:
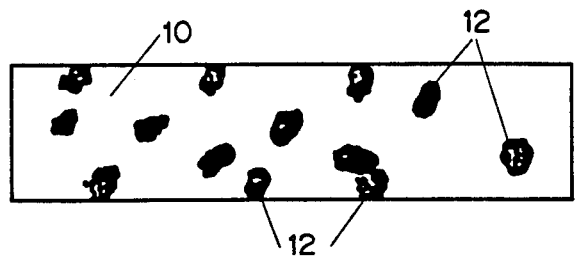
FIG. 1 is a schematic of the distribution of nueroactive substances within the polymeric drug delivery devices of the present invention, FIG. 1A showing that the drug is largely trapped by the surrounding polymer when present at a low concentration.
FIG. 1B showing that almost all of the drug is connected to the surface of the polymer via other drug particles, when present at higher concentrations, and is therefore releasable.
FIG. 1C showing an enlarged view of the pores in the polymer through which the diffusing drug must pass.
Figure 1B:
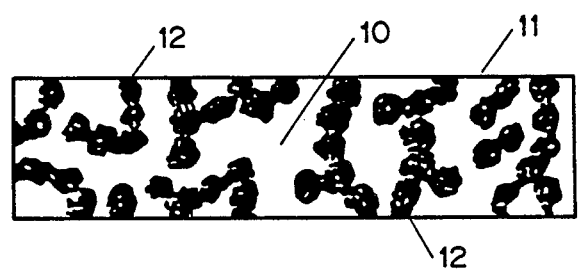
Figure 1C:
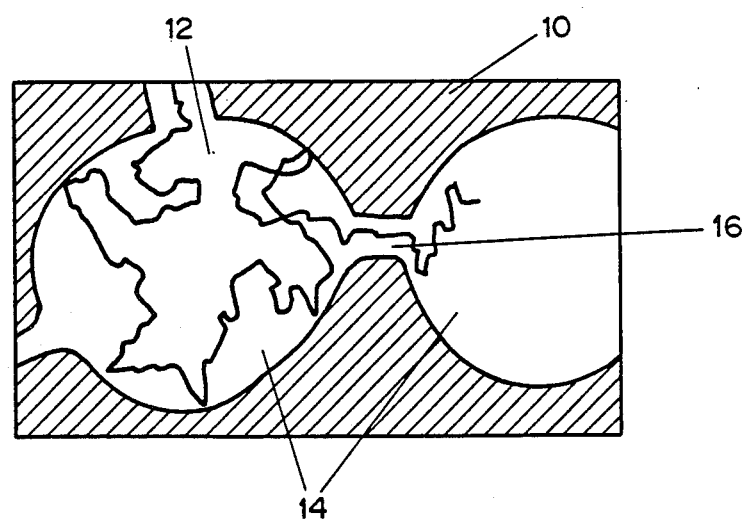

EVA can be used as a drug matrix in the controlled delivery system of the present invention. The advantage of matrix systems, as opposed to reservoir type slow release technologies, are their low price and relative safety in case of leakage. The drug is incorporated into the polymer as described below. Appropriate incorporation of the drug causes the formation of a series of tortuous interconnecting pores that can permit continuous release of both large and small molecules. FIG. 1 is a schematic of the distribution of nueroactive substances within the polymeric drug delivery devices of the present invention. The drug loading plays a key role in determining whether it is released in a linear fashion. FIG. 1A shows that the drug 12 is largely trapped by the surrounding polymer 10 when present at a low concentration; FIG. 1B shows that almost all of the drug 12 is connected to the surface 11 of the polymer 10 via other drug particles 12 when present at higher concentrations and is therefore releasable. FIG. IC is a schematic of the pores 14 in the polymer 10 through which the diffusing drug 12 must pass. Bulging pores 14 are connected via narrow channels 16. Due to the narrowness of the channels 16, the drug molecule 12 has a difficult time finding its way into the next pore 14.

The linear release of the bioactive compound into the nervous system is crucial to the present invention, something which has not previously been achievable. When EVA containing a drug is freely exposed to an aqueous solution, it releases the drug quite rapidly in a non-linear fashion. The preferred way to achieve constant release rates over extended time periods using EVA, or other polymers which do not degrade linearly, is to form an impermeable barrier around the drug containing polymer, leaving open a small concavity in the center of the face from which the drug is released.

The present invention has a number of advantages over prior art methods and compositions for drug delivery in the treatment of nervous system disorders. These include the linear release of the drug which eliminates the problems of erratic drug levels in the patient's blood, and the alleviation of problems with patient compliance. Further, sustained, linear, controlled release alters both the local and systemic concentrations and total dosage required, usually allowing a lower dosage of the drug to be given, decreasing side effects and the cost of treatment and allowing one to use more toxic compounds than would otherwise be possible.

There are a variety of compounds having an effect on nervous system disorders which can be incorporated into polymers for sustained release according to the present invention. Examples include neurohumoral agents, neurotransmitters such as acetylcholine, compounds which modify the quantity or activity of the neurotransmitters, and antagonists and agonists of these neurotransmitters.

The release of neuroactive compounds from hydrophobic ethylene-vinyl acetate copolymer (EVA) matrices according to the present invention has been demonstrated in vitro and in an animal model. Low molecular weight, neurally active substances, L-dopa, dopamine and $G_{M1}$ gangliosides, were encapsulated in the EVA polymer by solvent casting, as follows. Between 10 and 50% neurally active substance was homogeneously suspended in a solution of 10% (w/v) EVA in an organic solvent such as methylene chloride. This solution was cast in a glass mold at $-80°$ C. and the solvent was evaporated to produce a thin slab of drug-enriched material. Small pellets were cut from the slab. The pellets were either used immediately or coated with additional polymer to form rate controlling membranes. The method for determining how and to what extent rate controlling membranes are required for a particular polymer and drug mixture is demonstrated below.

Devices permitting the controlled release of neurally active substances could as easily be fabricated from non-erodible hydrophobic polymers other than EVA including polyvinyl acetate and polymethacrylate. Alternatively, controlled release could be achieved by encapsulating the drug in a bioerodible polymer: biologically inert material that slowly dissolves in the body to release the incorporated drug. Examples of these polymers are polyanhydrides, polylactic acid, polyglycolic acid, and polyorthoesters. Other than some of the polyanhydrides, these polymers do not degrade linearly over time. As a consequence, they must be formed in a particular shape, size, and with a rate controlling covering to result in linear release. It is preferable in some situations to use a non-erodible polymer where modifications or removal after implantation are necessary.

In general, these polymers must be carefully selected for use with the drug to be delivered, a method of encapsulation which does not decrease the bioactivity of the drug, lack of reactivity with the drug, the area of the nervous system where it is to be implanted, and the time over which the drug is to be released. The polymer must then be fashioned into the appropriate physical shape for implantation and linear release. The advantage of using EVA as the polymer base is that it is not only approved by the FDA for human use, but it has been shown that it can be used to generate linear, concentration and time-dependent release of small molecular weight, neurally relevant substances such as dopamine or choline over an extended period of time both in vitro and in vivo.

The drug-polymer compositions can be modified by the inclusion of other drugs or by altering the size, geometry, configuration, and other physical parameters of the polymer. EVA can also be manufactured such that the rate of release can be controlled from outside the body. In this system, both the drug and small magnetic beads are uniformly dispersed within the polymer. Upon exposure to an aqueous medium, drug is released as in the normal EVA system. However, when exposed to an oscillating magnetic field, drug is released at a much higher rate. Ultrasound can be used in a similar manner to increase the rate of release without altering the linearity.

The method for designing and constructing polymer-drug compositions for linear release of a representative neuroactive substance, L-dopa, is as follows. Ethylene vinyl acetate slabs containing 0%, 30%, 40% and 50% dopamine by weight formed by solvent casting as previously described were punched out to form round discs, approximately 3.0 mm in diameter. These discs were then coated by an additional layer of ethylene vinyl acetate either (i) completely; (ii) completely except for one concave pinhole present on one surface (iii) completely except for two concave pinholes present, one on each surface; (iv) partially, with one surface coated and the other not coated; or (v) not coated at all.

The release of dopamine into 5 ml of a 150 mM NaCl, 0.2% EDTA solution was monitored by measuring the absorbance at 280 nm of the solution at various time points and by comparison to a linear standard curve comparing absorbance at 280 nm to concentration of dopamine in the same buffered solution. The results are portrayed as either the absolute mass released over the time course of 65 days or as the amount of dopamine released as a fraction of the total amount present in the pellet.

Figure 2A:
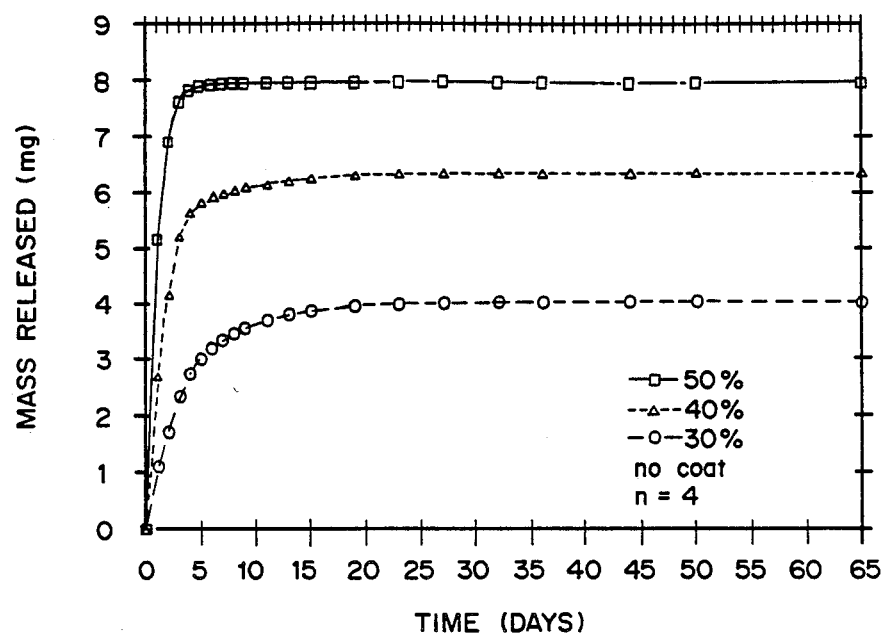
FIG. 2 are graphs of the release of dopamine from uncoated EVA pellets containing 30%, 40% or 50% dopamine, FIG. 2A showing the absolute amount of dopamine released and FIG. 2B showing the fraction of total dopamine present in the disc that is released.
Figure 2B:
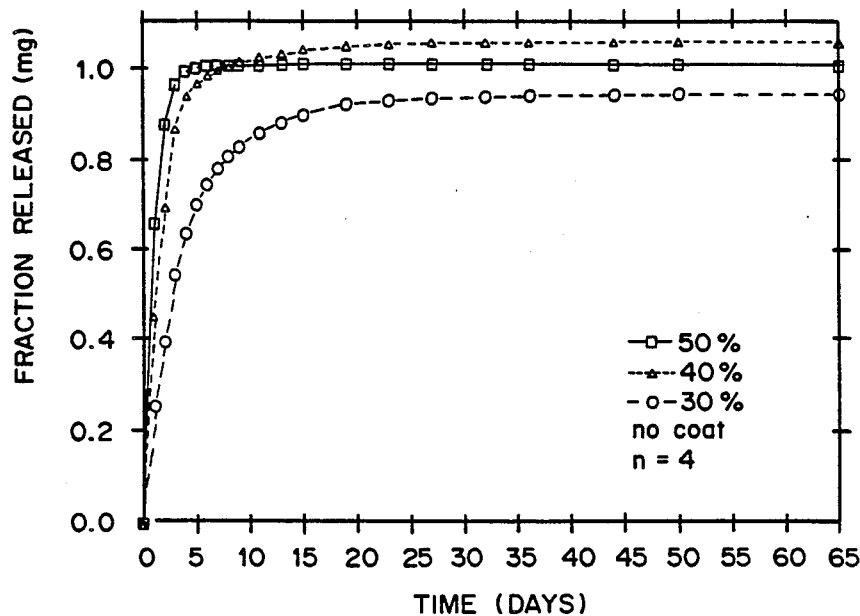

FIGS. 2A and 2B show the amount of dopamine released when the disc was not coated and contained 30%, 40% or 50% dopamine. In the absence of a coating, release occurred rapidly, in a non-linear manner.

Figure 3A:
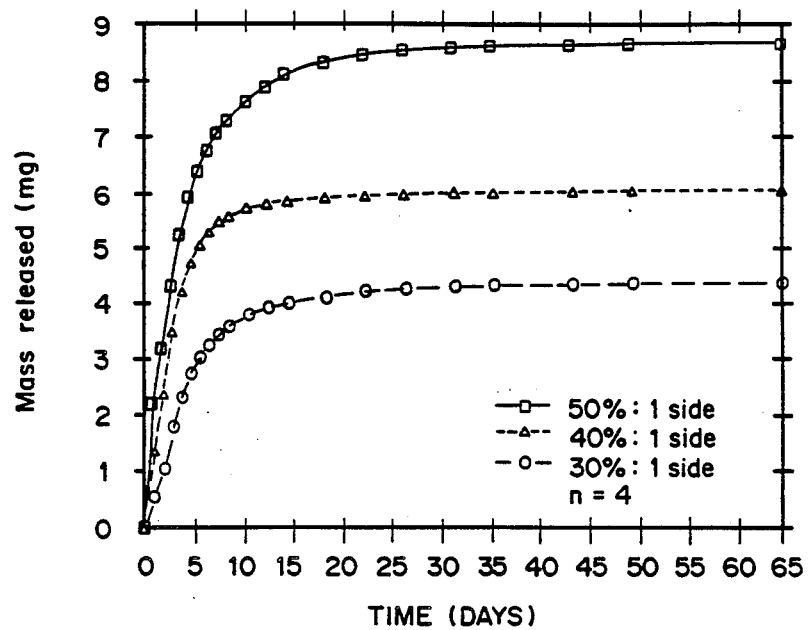
FIG. 3 are graphs of the release of dopamine from discs containing 30%, 40% or 50% dopamine coated only on one side, FIG. 3A showing the absolute amount of dopamine released and FIG. 3B showing the fraction of total dopamine present in the disc that is released.
Figure 3B:
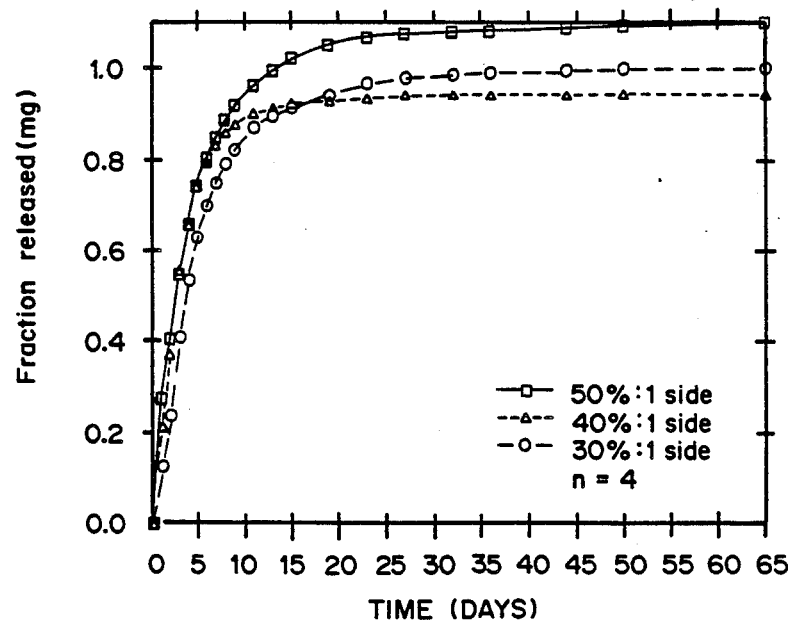

FIGS. 3A and 3B show the amount of dopamine released when the disc was coated on one side and contained 30%, 40% or 50% dopamine. The presence of a coating on one side tends to make the release curves somewhat more linear than in FIGS. 2A and 2B, although the release is not linear.

Figure 4A:
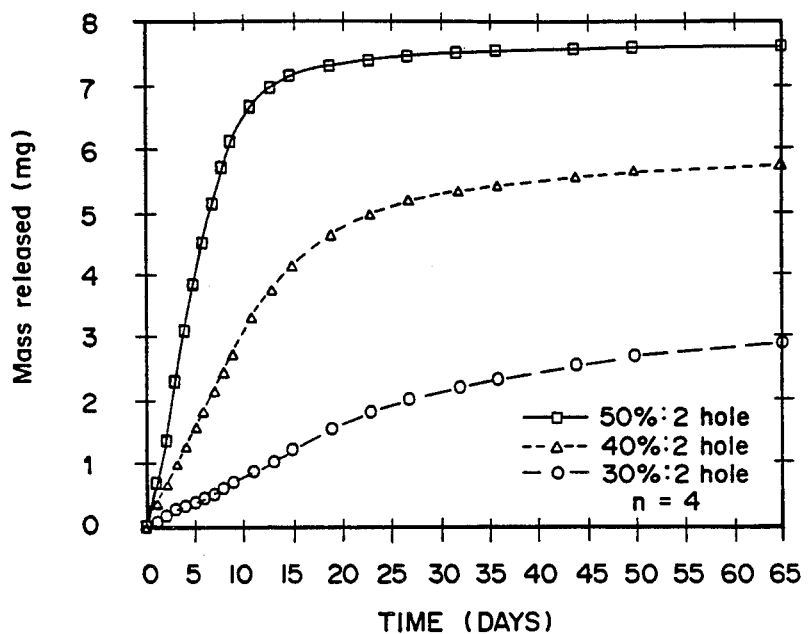
FIG. 4 are graphs of the release of dopamine from discs containing 30%, 40%, or 50% dopamine where the disc was fully coated except for two holes, one on each surface of the disc, FIG. 4A showing the absolute amount of dopamine released and FIG. 4B showing the fraction of total dopamine present in the disc that is released.
Figure 4B:
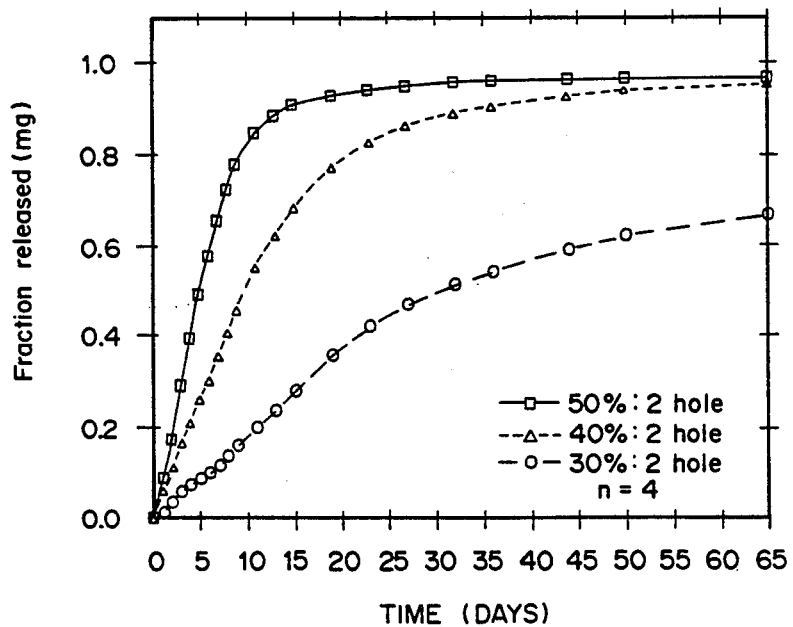

FIGS. 4A and 4B show the amount of dopamine released when the disc was fully coated except for two holes, one on each surface of the disc. These results show that a full coating except for two holes further linearizes the release. Virtual linear release is seen for the 30% loading.

Figure 5A:
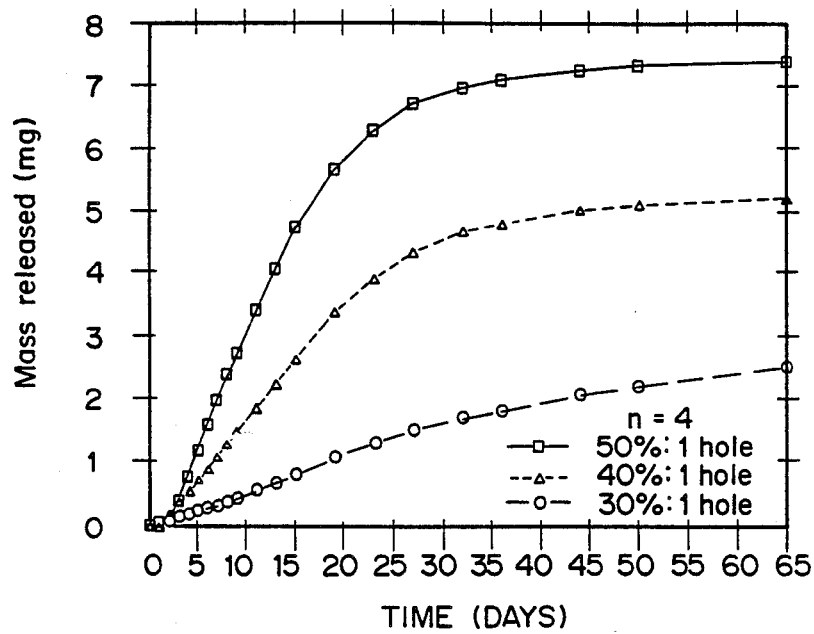
FIG. 5 are graphs of the release of dopamine from fully coated discs, except for the presence of one hole, containing 30%, 40%, or 50% dopamine, FIG. 5A showing the absolute amount of dopamine released and FIG. 5B showing the fraction of total opamine present in the disc that is released.
Figure 5B:
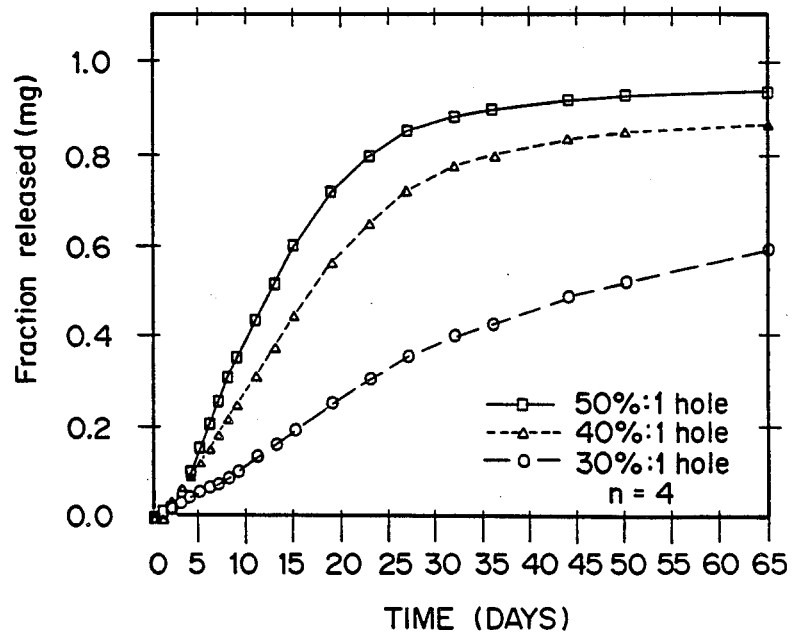
Figure 6A:
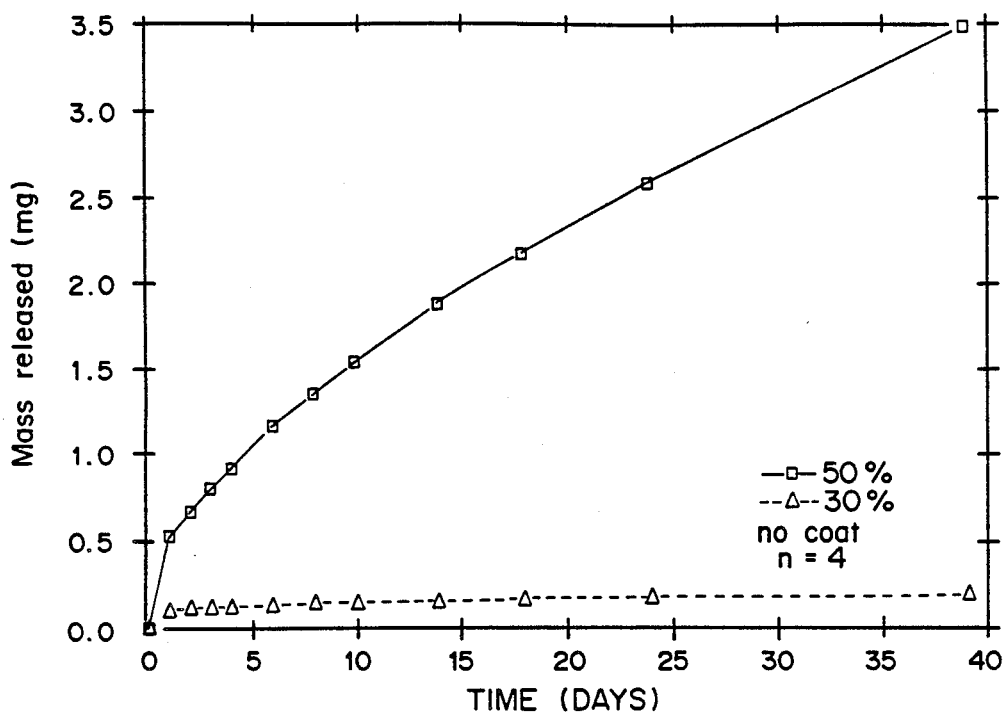
FIG. 6 are graphs of the absolute amount of L-dopa released from 3.0 mm round EVA discs containing 30% or 50% L-dopa by weight, FIG. 6A showing the amount released when the disc was not coated, FIG. 6B showing the amount released when the disc was coated on one side only, FIG. 6C showing the amount of L-dopa released when the disc was fully coated except for two holes, one on each flat surface of the disc, and FIG. 6D showing the amount of L-dopa released when the disc was coated fully except for one hole on one surface.
Figure 6B:
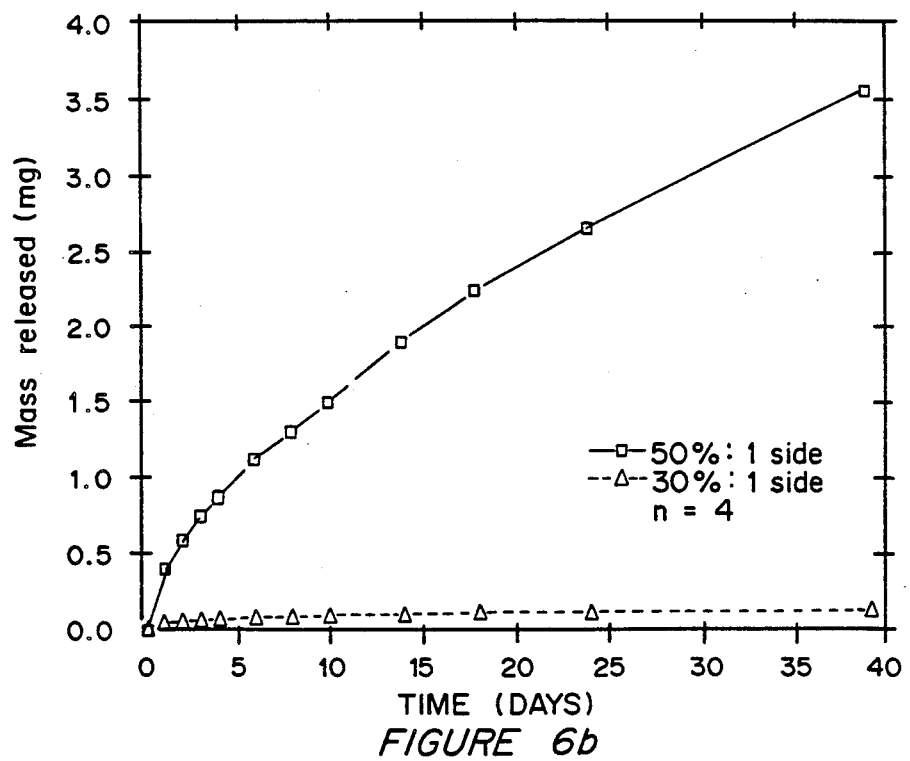
Figure 6C:
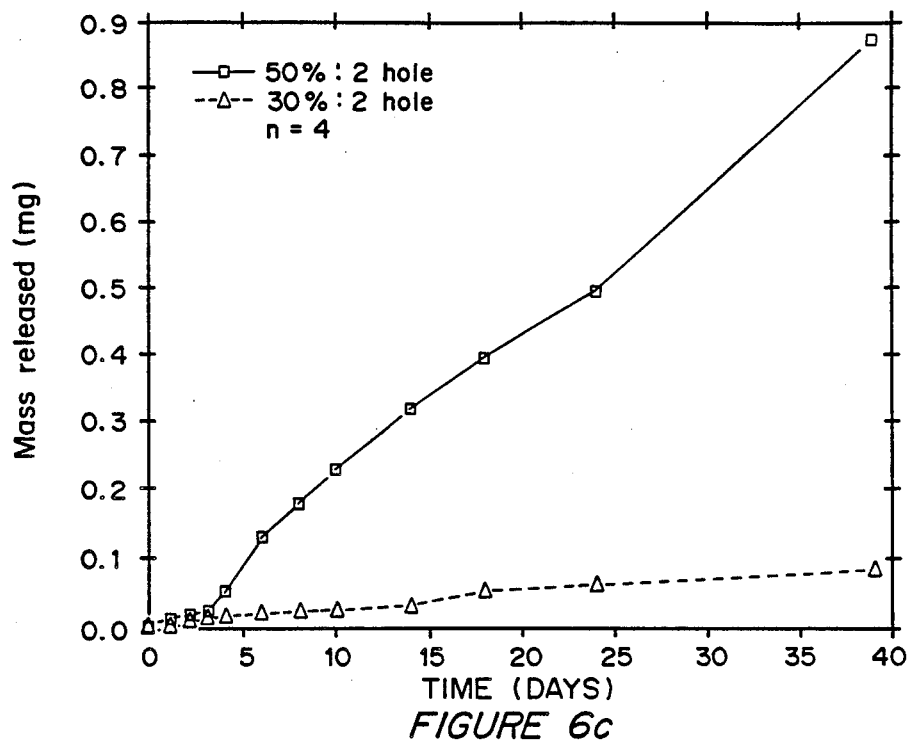
Figure 6D:
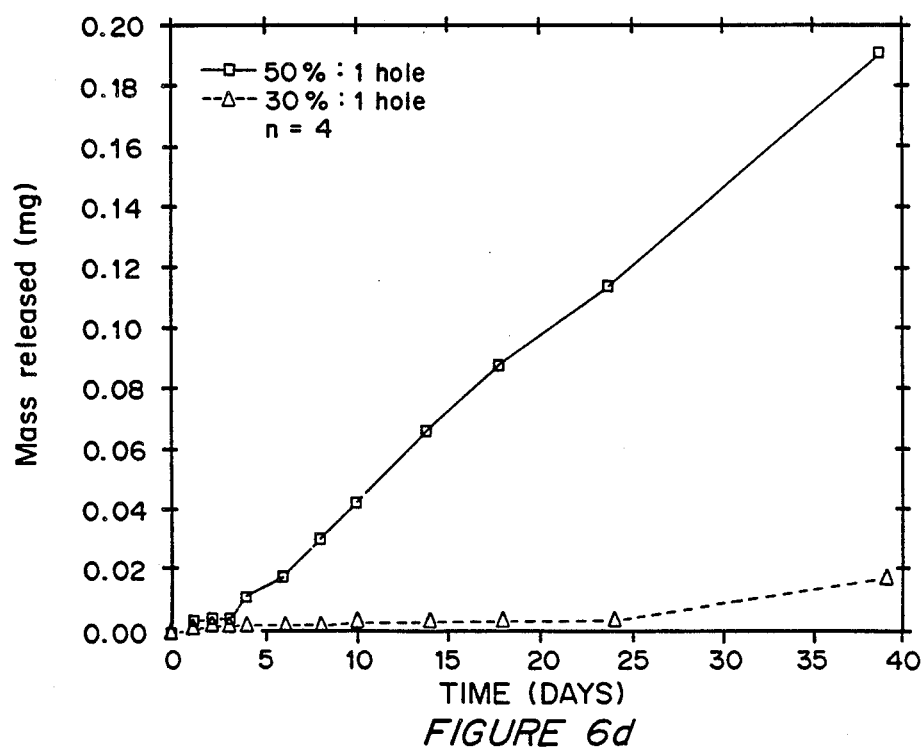

FIGS. 5A and 5B show the amount of dopamine released over 65 days when the disc was coated fully except for one hole. These results clearly demonstrate linear release at the 30% loading for up to 65 days in vitro. The release of dopamine from the discs containing 40% dopamine by weight, coated fully except for the presence of one hole, was also measured every thirty minutes over the course of several hours, to demonstrate that the initial release, as well as the long term release, is also linear. The results show that the release is constant and the deviation from one sample to the next minimal.

It is important to note that no release of dopamine was seen throughout the time period if the disc contained no dopamine (0% loading) or if the disc, containing 30%, 40% or 50% dopamine, was fully coated.

Samples of these solutions were injected into High Pressure Liquid Chromatography system designed to measure absolute quantities of dopamine and to distinguish dopamine from its oxidation products or other metabolites. The substance released was greater than 99.9% dopamine and the amounts measured were comparable to the amounts monitored by spectrometry.

Similar results were seen when the polymer base was a polyanhydride rather than ethylene vinyl acetate.

Another neuroactive substance, $G_{M1}$ 'ganglioside (95% purity, Fidia Research Laboratories), was imbedded in EVA using the solvent casting technique. The solvent system was methylene chloride. The drug loading was: 50%: 0.7 g EVA and 0.7 g $G_{M1}$; 40%: 0.7 g EVA and 0.47 g $G_{M1}$; 30%: 0.7 g EVA and 0.3 g $G_{M1}$. After freeze-drying the polymer-$G_{M1}$ mixture, round pellets measuring 3 mm in diameter and 1 mm in depth were cut out of the slab. These were either coated with pure ethylene vinyl acetate or left uncoated. Coated pellets either had one side exposed or contained one or two holes punched in the coating using a 16 gauge needle. Control pellets were either fully coated or contained no $G_{M1}$.

The final approximate weight of the pellets were 135 mg (50%), 125 mg (40%), and 100 mg (30%). Quadruplicates of each pellet type were tested individually.

Release of $G_{M1}$ from each EVA pellet was measured by its release into scintillation vials containing 5 ml of physiological buffer (Krebs buffer without glucose). The vials were kept in a water bath at 37° C. under constant agitation. $G_{M1}$ content of 0.5 and 1.0 mls aliquots were measured by reacting the solution with resortinol and measuring the content of n-acetyl-neuraminic acid (NANA) in a spectrophotometer.

Figure 7A:
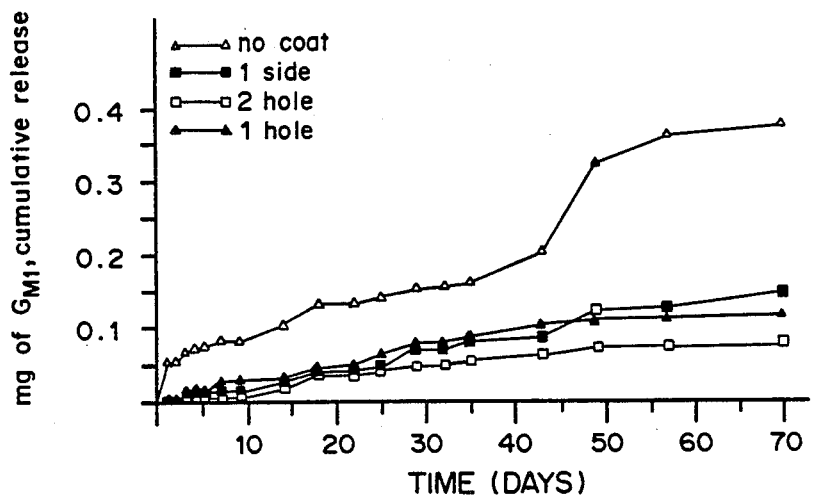
FIG. 7 are graphs of the release of $G_{M1}$ gangliosides from 3.0 mm round EVA pellets over a 70 day period, comparing the release from pellets with no coating, pellets coated on only one side, pellets coated with a hole of each surface and pellets coated with a hole on only one surface, for pellets containing 30% loading of $G_{M1}$, shown in FIG. 7A, pellets containing 40% loading of $G_{MI}$, shown in FIG. 7B, and for pellets containing 50% loading of $G_{M1}$, shown in FIG. 7C.
Figure 7B:
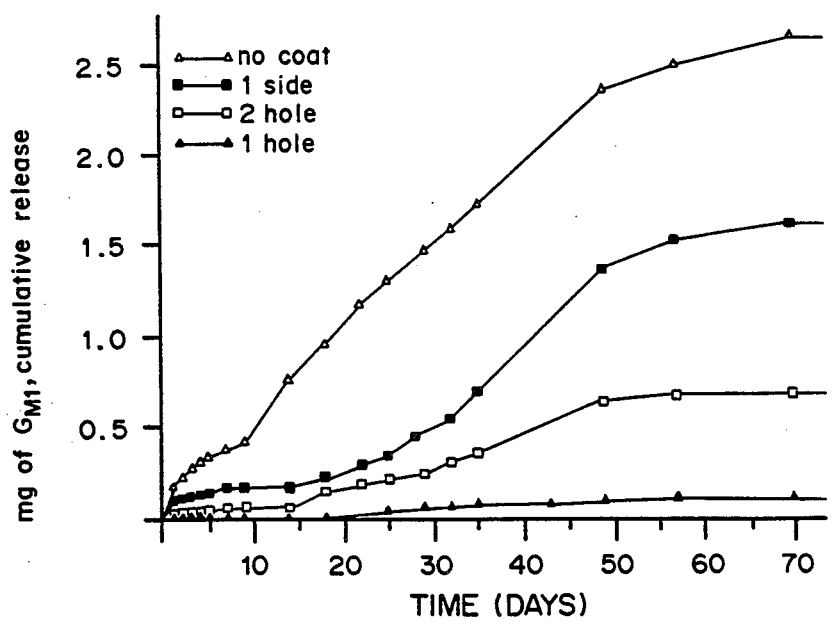
Figure 7C:
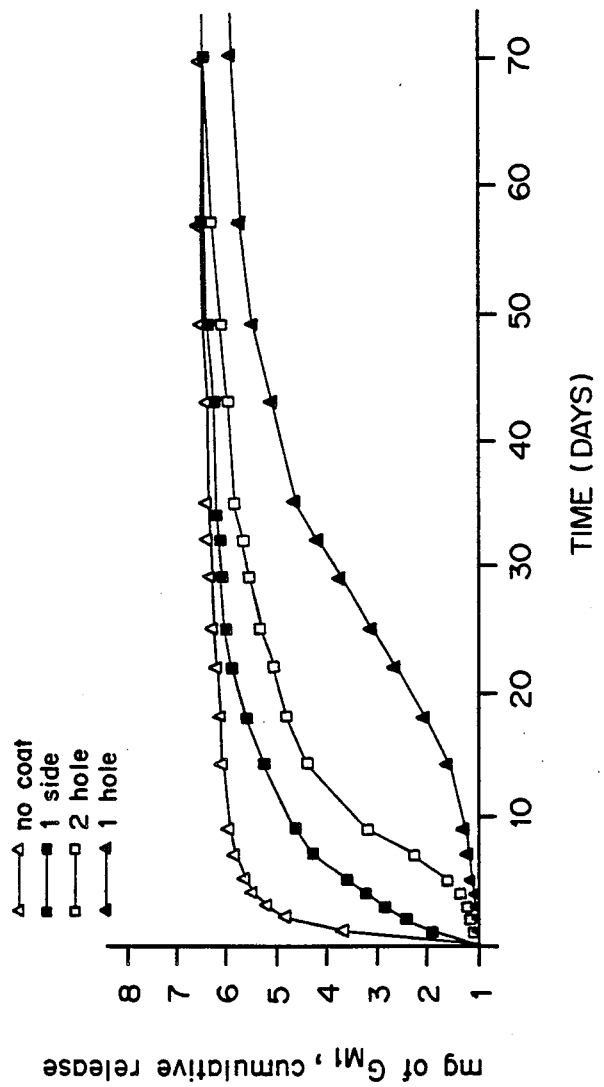

The release of 30%, 40%, and 50% $G_{M1}$ from the EVA pellets over a 70 day period is shown in FIG. 7A, 7B and 7C, respectively. Those pellets with a full coating or no $G_{M1}$ showed no measurable release of $G_{M1}$. The maximum cumulative release of $G_{M1}$, i.e. the total release, and the release efficiency, expressed as percent of loading, are shown in Table I. The results show that the release efficiency increases with increased loading and suggests that higher loading will permit more rapid release. It is also clear that linear release occurs only under certain geometric configurations, for example, the 40% loading with no coat and the 50% loading with a full coat except one hole.

TABLE I

| RELEASE OF $G_{M1}$ FROM EVA PELLETS | | | |
|---|---|---|---|
| Loading (% w/w) | GM1 content (mg) | Total release (mg) | % release (%) |
| 50 | 65 | 6.0 | 9.0 |
| 40 | 52 | 3.0 | 5.8 |
| 30 | 30 | 0.4 | 1.3 |
| 0 | 0 | 0 | 0 |

The present invention is further described by the following demonstrations of in vivo release of dopamine from EVA pellets implanted in rats. In the first example, intracerebral dialysis was used to monitor extracellular levels of dopamine in the striatum of pentobarbitone anaesthetized rats. In the second example, behavior was correlated with release of dopamine from implanted EVA pellets.

The Neurosurgical Implantation of Dopamine Containing Ethylene-Vinyl Acetate Pellets into the Brains of Male Sprague-Dawley Rats: ECF Dopamine Levels.

Male Sprague-Dawley Ras (150-200 g) were anaesthetized with pentobarbitone (60 mg/kg) and placed in a David Kopf stereotaxic frame. The skull was exposed and a 4 mm diameter hole drilled centered at coordinates A +0.4 mm and R 2.6 mm using the Paxinos and Watson coordinates. The right cortex was aspirated using a mild vacuum down to the striatal surface (ventral - 3 mm). Pellets were implanted with the uncoated pore, when present, facing ventrally and imbedded in the body of the striatum. Both control, non-dopamine containing pellets, and dopamine containing (2 mg) pellets were implanted. In vivo release was measured on the third, twentieth and sixty-fifth days. Intracerebral Dialysis Method:

Rats were anaesthetized with pentobarbitone (60 mg/kg) and placed in the Kopf stereotaxic frame. The skull was exposed and a Carnegie Medicin dialysis probe (4 mm membrane length, 0.5 mm o.d., 5,000 m.w. cut off) implanted into the striatum at Paxinos and Watson coordinates A +2.1, R (or L) 1.9, V −7 mm. Probes were perfused with an artificial CSF medium, 1 mM Ca, pH 7.35, at a flow rate of 1.5 microliter/min using a CMA 100 pump. Fifteen minute samples were collected into 5 microliters of 0.5M perchloric acid. The probe was calibrated by measuring the recovery of standards of known concentration, 100 nM. Dialysates were immediately assayed by direct injection onto a highly sensitive reverse-phase, isocratic HPLC with an ESA 5100 coulochem detector. Chromatograms were completed within 11 minutes. After an initial period of "injury release", 60 to 90 minutes post probe implantation, stable concentrations of dopamine were measured for a minimum of three 45 min collections.

The first rat had probes inserted into the right striatum on the third and sixty-fifth days and in the left striatum on the sixty-fifth day post polymer implantation. The second rat had probes inserted into both the right and left striata on the twentieth day. The third, control rat had a probe inserted into the right striatum on the third day.

On the third day, the basal dopamine concentration in the extracellular fluid (ECF) of the right striatum of the first rat was 28 nM. The basal dopamine concentration in the right striatum ECF of the control rat was 22 nM. The basal dopamine concentration in the right (implant side) striatum of the second rat was 6,230 nM. The dopamine concentration on the left side was 30.5 nM.

On the sixty-fifth day, the basal dopamine concentration of the right striatum of the first rat was 7,200 nM. The level on the left was 36 nM.

In both dopamine implant rats, the dopamine concentrations in the left striatum were the same as the dopamine level in the right striatum of the control polymer rat. The 22, 30.5 and 36 nM concentrations are within the normal range of dopamine values that have been reported in untreated animals of 29±8 nM by Dr. Matthew During at the Massachusetts Institute of Technology, Cambridge, Mass. The level of dopamine in the right striatum on the third day was also unchanged from normal at 28 nM. In contrast, the values in the right striatum seen on the twentieth and sixty-fifth days of 6,230 and 7,200 nM represent more than a 200 fold increase in dopamine levels. ECF concentrations of this order have not been previously reported even with treatments such as amphetamine nor high potassium in a perfusate and ischaemia which cause massive release of dopamine. There is no doubt therefore that these results reflect a major release of dopamine into the extracellular fluid of the implanted striatum, that such release is not evident on the third day, but is seen by the twentieth day and persists for at least two months.

The Neurosurgical Implantation of Dopamine Containing Ethylene-Vinyl Acetate Pellets into the Brains of Male Spraque-Dawley Rats: Behavioral Correlation Three 350 g male Sprague-Dawley rates were anesthetized by i.p. injection of 50 mg nembutal/kg and 0.1 cc atropine. The fur was then shaved from their heads and each rat placed in a Kopf sterotaxic device. Using an Emesco Drill and an American Optical scope, the skull was carefully removed in a 5 mm ×5 mm square centered 1.5 mm anterior to the bregma and 3 mm lateral to the midline suture on either side. Cortex was carefully suctioned out, as well as corpus callosum, until the surface of the striatum could be seen. Then, in a blind manner, the surgeon implanted pellets into each side of the brain.

The first rat had a coated pellet containing 20% dopamine implanted on the right side, and an EVA pellet control, containing no other substances, implanted on the left. The second rat had the dopamine pellet implanted on the left side and the control pellet implanted on the right. The third animal had three 4 mm ×0.5 mm ×0.5 mm strips of uncoated dopamine-containing (20%) EVA implanted within the corpus striatum in the left hemisphere, and a control pellet on the right side.

After recovery from surgery, the animals were placed in a rotometer which can measure the number of turns in each of two directions (clockwise or to the right; counterclockwise or to the left). The ratio of turns to the right and turns to the left are reported and indicative of rotation in a preferred direction. The results are presented in Table II. The implantation of the ethylene vinyl acetate polymer containing dopamine induces rotation to the contralateral (opposite) side when implanted on one side of the brain, in or above the corpus striatum, which is the expected behavior due to an increase in dopamine release.

TABLE II

Rotometer Values of Dopamine-EVA Polymer Implanted Rats (Right:Left)

| | Time: | | | |
|---|---|---|---|---|
| | zero h | 10 h | 16 h | 32 h |
| Rat 1 | 0:0 | 62:265 | 91:370 | 205:490 |
| Rat 2 | 0:0 | 28:0 | 52:4 | 243:90 |
| Rat 3 | 0:0 | 1548:106 | 1940:148 | 4860:252 |

In a similar fashion, L-dopa/carbidopa can be encapsulated in EVA and implanted subcutaneously into Parkinsonian patients. Peripheral implants employing EVA or similar polymers are expected to provide constant, rather than phasic, levels of exogenously supplied L-dopa. It is reasonable to expect that patients with such implants would have a more stable reduction of symptoms as well as more constant mood states. Drugs can be released from the EVA polymeric devices of the present invention at a constant rate over several months and up to a year. Compliance is a problem since many Parkinson's patients are depressed and have cognitive deficits. Polymer implants would avoid this problem since the implant treatment does not require patient participation.

Further, there is a strong possibility that constant but low levels of L-dopa may circumvent the development of undesirable side-effects associated with the traditional approach. It is now quite clear that the pulsatile drug level of traditional therapies is directly related to the appearance of undesirable side-effects of L-dopa therapy. Continuous, slow infusion of L-dopa by intravenous lines has been demonstrated to be advantageous for the treatment of Parkinson's disease, especially in cases with complicated response swings, by N. Quinn, et al, Dept. of Neurology, Inst. of Psychiatry, de Crespigny Park, Denmark Hill, London, SE5 8AF, England, as reported in the Lancet 2:412–415 (Aug 21 1982). Three Parkinsonian patients on oral levodopa treatment for 8 to 10 years, with complex fluctuations from 5 to 8 years, were given continuous i.v. infusions of levodopa. The results showed that the replacement of oral levodopa treatment produced a prolonged and stable clinical response. It was concluded that in patients with complicated response swings, central dopamine receptors remain available for stimulation providing levodopa can be delivered at a constant rate and in an adequate quantity to the brain. Thus, using slow release technology for treatment of Parkinsonian patients would not only maintain more constant moods and symptoms, but would reduce side-effects, thus eliminating the need for drug holidays.

Polymeric drug delivery devices could also be implanted intracerebrally (directly into the brain) into patients with Parkinsonism. These implantations would be useful in the treatment of cases refractory to conventional methodologies, where the patients have a complete loss of nigral neurons; where precise targeting of the drug to a desired location within the brain is desirable; and where it is desirable to avoid ethical and other ramifications present with fetal or tissue implants. Since transmitters such as dopamine act non-specifically, dopamine could be precisely targeted by polymer implants to elevate the tonic level of transmitter in the caudate nucleus after total destruction of the substantia nigra.

The method and compositions described above are equally applicable to other neurological disorders. Examples are Alzheimer's Disease and Huntington's Chorea. In Alzheimer's dementia, the predominant pathology is a depletion in the levels of the transmitter acetylcholine. An animal model of Huntington's Disease was recently used to assess the effects of fetal cholinergic brain transplants. Both of these diseases are likely to prove to be ameliorable with artificial implants which slowly release transmitters or transmitter agonists or antagonists. Essentially any transmitter, its precursor, its agonist or its antagonists can be entrapped into the appropriate polymer using methods known to those skilled in the art, formed into the appropriate shape and implanted in an area targeted to allieviate symptoms.

Intracerebral implants containing substances that would otherwise not pass the blood brain barrier have potential use as therapies for hitherto untreatable disorders. For example, intracerebral implants containing large molecular weight molecules, such as many of the proteins, may be useful for treating metabolic disorders for which no effective therapy exists as yet. One such case is a class of disorders collectively referred to as "lysosomal storage diseases", and includes the inherited Tay Sachs or Gaucher's diseases. In such diseases, the brain lacks certain functional enzymes which are needed for the breakdown of otherwise toxic compounds such as gangliosides and cerebrosides. Treatment of enzyme deficiencies in man with injections of enzymes, isolated from human or animal sources, outside of the nervous system is normally associated with a host of problems. In addition to the immunological reaction which can both destroy the administered enzyme and harm the patient, there is the possibility of undesirable enzyme action on substrates in areas other than those in need of therapy. Furthermore, enzymes are prone to premature inactivation in non-target extracellular and intracellular regions before reaching the blood brain barrier which they then cannot pass. A controlled release of such enzymes from polymer brain implants offers a unique opportunity to specifically target the enzyme into the affected areas of the brain, diminishing levels of toxic accumulated metabolites and restoring normal neuronal function.

Another important application of the polymeric drug delivery devices of the present invention is in the treatment of depression. Depression strikes one out of every ten Americans at one point in their life. It is usually treated with antidepressants such as tricyclics and MAO inhibitors, in conjunction with psychotherapy. The phasic nature of conventional administration of these drugs presents a number of problems. In addition, patient compliance by severely depressed patients is a particularly troublesome problem. Polymer implants containing antidepressants would eliminate these and other problems of existing therapies. In schizophrenia, which is treated with antipsychotics, patient compliance is so poor that the patient must often be hospitalized merely to administer the drug. The polymeric implants also address this disorder and may reduce the likelihood of toxic side-effects due to long term, high dosage therapy, such as tardive dyskinesia.

There are a variety of potential applications of slow-release technology to neuroscience research. One of these applications is in tissue culture work. A major problem of in vitro research is the fact that the substrates for transmitters are used up or inactivated over time. Many studies, such as those investigating biochemical and physiological responses to long term exposure to neuromodulatory agents, are limited by the absence of a continuous, consistent and inexpensive method of delivering compounds. One application is in the use of tissue cultures in the neuroscience area. A polymeric device could be placed into a tissue culture dish for release of one or several of a variety of compounds, such as neurotransmitters, growth factors, and chemotactic agents. These research applications could have similar use in alleviating the problems in the industrial scale production of pharmaceuticals or chemicals by large mammalian cell fermenters which often require constant levels of growth factors.

There are also a variety of in vivo research applications of slow release technology for the neurosciences. Included among these are the investigation of behavioral and physiological effects of one or several transmitter(s) released slowly into a specific brain area. Although tissue transplants are being used extensively for this research, there are enormous limitations in the interpretation of the results, particularly since it remains unclear how the transplants in fact work.

Modifications and variations of the present invention, a method and compositions for treating neural disorders, will be obvious to those skilled in the art of treating neural disorders from the foregoing detailed description. Such modifications and variations are intended to come within the scope of the appended claims.

We claim:

1. A method for treating disorders of the nervous system comprising: Selecting a compound which stimulates or replaces a specific function of components or the nervous system selected from the group consisting of L-dopa, dopamine, carbidopa, choline, acetyl choline, cholinergic neuronotropic agents, gangliosides, nerve growth enhancing agents, antipsychotropic agents, antidepressants, excitatory amino acid antagonist or agonist, antiepileptic medications enzymes and combinations thereof; selecting a biocompatible polymer; encapsulating said compound within said polymer to form a polymeric device having at least one opening at the surface, wherein said compound is linearly released from said polymeric device over a sustained period of time greater than three months at a predetermined level and rate to the nervous system.

2. The method of claim 1 further comprising implanting said polymeric device at a location within a patient wherein the release of said compound produces a desired effect on the patient.

3. The method of claim 1 wherein said polymer is selected from the group of bioerodible polymers consisting of polyanhydrides, polylactic acid, polyglycolic acid, polyorthoesters, and combinations thereof.

4. The method of claim 1 wherein said polymer is selected from the group of polymers consisting of ethylene vinyl acetate, polyurethanes, polystyrenes, polyamide, polyacrylamide, and combinations thereof.

5. The method of claim 1 wherein the polymer is selected to control the rate of release of said compound.

6. The method of claim 1 further comprising forming said polymer around said compound in a thickness and with a specific area calculated to provide sustained, linear release over a predetermined period of time.

7. The method of claim 1 wherein said compound is selected from the group of compounds consisting of L-dopa, dopamine, carbidopa, choline, acetylcholine, cholinergic neuronotropic agents, gangliosides, nerve growth enhancing agents, antipsychotic agents, antidepressants, excitatory amino acid antagonists and agonists, antiepileptic medications, antibiotics, enzymes, anti-viral agents, and combinations thereof.

8. The method of claim 1 for treating Parkinson's disease wherein said compound is selected from the group consisting of L-dopa, carbidopa, and dopamine.

9. The method of claim 1 for treating nervous system injury wherein said compound is gangliosides.

10. The method of claim 1 for treating Alzheimer's Disease wherein said compound is a cholinergic agonist, antagonist or neuronotrophic agent.

11. The method of claim 1 for treating multiple sclerosis wherein said compound is beta-interferon.

12. The method of claim 1 for treating Huntington's Disease wherein said compound is an antagonist of excitatory amino acids.

13. The method of claim 1 wherein said encapsulated compound is implanted within the brain.

14. The method of claim 1 wherein said encapsulated compound is implanted immediately adjacent the peripheral nervous system.

15. The method of claim 1 further comprising forming a second, impermeable polymer surface on said polymeric device and creating discrete openings in said second surface to control the rate and level of release.

16. A composition for treating disorders of the nervous system comprising:
a compound which stimulates or replaces a specific function of components of the nervous system selected from the group consisting of L-dopa, dopamine, carbidopa, choline, acetylcholine, cholinergic neuronotrophic agents, gangliosides, nerve growth enhancing agents, antipsychotropic agents, antidepressants, excitatory amino acid antagonists or agonists, antiepileptic medications, enzymes, and combinations thereof;
a biocompatible polymer matrix;
wherein said compound is encapsulated within said polymeric matrix, said polymeric device having at least one opening at the surface allowing access of liquid at the treatment site to the compound, wherein the compound is linearly released over a sustained period of time in excess of three months in a predetermined amount and rate through the opening as the compound dissolves into the liquid entering the device through the opening. and areas where the compound has dissolved within the polymeric device.

17. The composition of claim 16 further comprising a second impermeable biocompatible polymer surface, said second surface having discrete openings to control the rate and level of release of said compound.

18. The composition of claim 16 wherein said polymer is selected from the group of bioerodible polymers consisting of polyanhydrides, polylactic acid, polyglycolic acid, polyorthoesters, and combinations thereof.

19. The composition of claim 16 wherein said polymer is selected from the group of polymers consisting of ethylene vinyl acetate, polyurethanes, polystyrenes, polyamide, polyacrylamide, and combinations thereof.

20. The composition of claim 16 wherein the polymer composition affects the rate of release of said compound.

21. The composition of claim 16 wherein said polymer is formed around said compound in a thickness and with a specific area calculated to provide sustained, linear release over a predetermined period of time.

22. The composition of claim 16 further comprising a compound selected from the group consisting of antibiotics, anti-viral agents and combinations thereof.

* * * * *